(12) United States Patent  (10) Patent No.: US 7,147,647 B2
Onyekaba et al.  (45) Date of Patent: Dec. 12, 2006

(54) SINTERED TITANIUM TUBE FOR THE MANAGEMENT OF SPINAL CORD INJURY

(75) Inventors: Chike O. Onyekaba, Coon Rapids, MN (US); George Johnstone, Brooklyn Center, MN (US); Dennis Elsberry, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 470 days.

(21) Appl. No.: 10/133,798

(22) Filed: Apr. 26, 2002

(65) Prior Publication Data

US 2003/0204197 A1  Oct. 30, 2003

(51) Int. Cl.
A61B 17/08 (2006.01)
(52) U.S. Cl. .................................................. 606/152
(58) Field of Classification Search ........ 606/151–155; 623/1.39, 1.4, 1.44; 424/422–424
See application file for complete search history.

(56) References Cited

U.S. PATENT DOCUMENTS

| | | | | |
|---|---|---|---|---|
| 2,127,903 | A | * | 8/1938 | Bowen ..................... 606/154 |
| 3,786,817 | A | | 1/1974 | Palma |
| 3,833,002 | A | | 9/1974 | Palma |
| 3,893,462 | A | | 7/1975 | Manning |
| 3,916,905 | A | | 11/1975 | Kuhn |
| 3,960,151 | A | * | 6/1976 | Kuhn ........................ 606/152 |
| 4,105,017 | A | | 8/1978 | Ryaby et al. |
| 4,306,561 | A | | 12/1981 | de Medinaceli |
| 4,534,349 | A | * | 8/1985 | Barrows ..................... 606/152 |
| 4,604,762 | A | * | 8/1986 | Robinson ................... 623/1.44 |
| 4,623,355 | A | | 11/1986 | Sawruk |
| 4,662,884 | A | | 5/1987 | Stensaas et al. |
| 4,669,474 | A | | 6/1987 | Barrows |
| 4,774,967 | A | | 10/1988 | Zanakis et al. |
| 4,778,467 | A | | 10/1988 | Stensaas et al. |
| 4,877,029 | A | | 10/1989 | Valentini et al. |
| 4,878,913 | A | | 11/1989 | Aebischer et al. |
| 4,919,140 | A | | 4/1990 | Borgens et al. |
| 5,011,486 | A | * | 4/1991 | Aebischer et al. .......... 600/152 |
| 5,030,225 | A | | 7/1991 | Aebischer et al. |
| 5,354,305 | A | | 10/1994 | Lewis et al. |
| 5,527,353 | A | * | 6/1996 | Schmitt .................... 623/1.44 |
| 5,925,053 | A | | 7/1999 | Hadlock et al. |
| 6,029,090 | A | | 2/2000 | Herbst |
| 6,132,360 | A | | 10/2000 | Halpern |
| 6,214,021 | B1 | | 4/2001 | Hadlock et al. |
| 6,440,455 | B1 | | 8/2002 | Benowitz |
| 6,487,450 | B1 | | 11/2002 | Peng-Sheng |
| 6,551,612 | B1 | | 4/2003 | Benowitz |
| 6,676,675 | B1 | * | 1/2004 | Mallapragada et al. ..... 606/152 |
| 6,824,538 | B1 | | 11/2004 | Peng-Sheng |
| 2002/0055484 | A1 | | 5/2002 | Benowitz |
| 2002/0137721 | A1 | | 9/2002 | Benowitz |
| 2002/0143365 | A1 | | 10/2002 | Herbst |

(Continued)

FOREIGN PATENT DOCUMENTS

EP  0261833  3/1988

(Continued)

*Primary Examiner*—Julian W. Woo
(74) *Attorney, Agent, or Firm*—Mary P. Bauman; Medtronic, Inc.

(57) ABSTRACT

A device and method for the treatment of damaged nerves and, more particularly, a tubular membrane having a microtextured surface for the treatment of central or peripheral nerve injuries. The microtextured surface of the tubular membrane inhibits the growth of fibrous tissue, which prevents the reattachment of nerve fiber ends.

17 Claims, 2 Drawing Sheets

U.S. PATENT DOCUMENTS

| | | |
|---|---|---|
| 2003/0028204 A1 | 2/2003 | Shu-Tung et al. |
| 2003/0109814 A1 | 6/2003 | Rummerefield |
| 2004/0214790 A1 | 10/2004 | Borgens |

FOREIGN PATENT DOCUMENTS

| | | |
|---|---|---|
| EP | 0327022 | 8/1989 |
| WO | WO 8403035 | 8/1984 |
| WO | WO 9203536 | 3/1992 |
| WO | WO 9312724 | 7/1993 |
| WO | WO 9937359 | 7/1999 |
| WO | WO 9965536 | 12/1999 |
| WO | WO 2002/062216 | 8/2002 |
| WO | WO 2002/092107 | 11/2002 |
| WO | WO 2003/000388 | 1/2003 |
| WO | WO 2003/041484 | 5/2003 |

* cited by examiner

SINTERED TITANIUM TUBE FOR THE MANAGEMENT OF SPINAL CORD INJURY

FIELD OF THE INVENTION

The present invention relates to a device and method for the treatment of damaged nerves and, more particularly, to a tubular membrane having a microtextured surface for the treatment of central or peripheral nerve injuries.

BACKGROUND OF THE INVENTION

It is known that after an injury to a central or a peripheral nerve, nerve regeneration depends on the elongation or regrowth of axons destroyed at the site of injury. Axon elongation or regrowth, however, is hindered by the structural and metabolic changes that occur at the site of the nerve injury. For instance, when a nerve is injured, nerve cells and blood vessels are destroyed with the release of serum, proteins, plasma fluid, cells, growth factors, and crushed tissue. In turn, the body recruits macrophage to clean the dead cell and blood vessel debris and clean the environment. In addition, macrophage release cytokines and other growth promoting factors to stimulate tissue repair.

In a long lasting injury, the tissue repair process progesses to a chronic stage where the body recruits fibroblasts to the site of the nerve injury. Fibroblasts release growth factors that help to recruit additional fibroblast to facilitate the repair process. This cycle leads to the buildup or overgrowth of exuberant fibrous tissue at the site of the nerve injury. Exuberant fibrous tissue overgrowth, however, prevents the nerves from interconnecting and regenerating, and hinders the axon and neuronal cells from proliferating. Consequently, a need exists for a device and method that prevents exuberant tissue overgrowth from impeding or interfering with the nerve regeneration or regrowth process.

In addition to the problems caused by exuberant tissue overgrowth, the axons have no guidance as they elongate during the repair process. Consequently, the axons elongate into a tangled web of unorganized axons. A need therefore exists for a device and method that provides axons guidance as they elongate during the repair process. The present invention overcomes the known problems encountered during the nerve regeneration process.

BRIEF SUMMARY OF THE INVENTION

The present invention relates to a device and method for treating damaged nerves. In a first embodiment, the present invention relates to a sintered titanium tubular membrane having a microtextured surface for the treatment of central or peripheral nerve injuries. In an exemplary embodiment, the tubular membrane has an inner surface, an outer surface, and two opposing ends. The inner and outer surfaces of the tubular membrane contain a textured topography that diverts exuberant tissue overgrowth away from the region or site of a nerve injury. In the exemplary embodiment, the textured surface contains a plurality of pores having diameters between 1–3 μm (microns) and depths of at least 0.5 μm (microns). In addition, the textured surface may include a plurality of microgrooves or channels that provide a path or guide for the axons as the axons elongate during the nerve repair process. The microgrooves or channels extend lengthwise along the tubular membrane and run parallel to each other. The microgrooves or channels have widths ranging from 1–3 μm and depths of at least 0.5 μm.

In a second embodiment, the present invention relates to the method of using the tubular membrane for treating damaged nerves. The method includes providing a tubular membrane having a textured surface including a plurality of pores having diameters between 1–3 μm and depths of at least 0.5 μm. The tubular membrane further includes a plurality of microgrooves or channels having widths ranging from 1–3 μm and depths at least 0.5 μm. The method also includes placing a damaged nerve within the tubular membrane, which facilitates regeneration of the damaged nerve by diverting fibrous tissue overgrowth into the plurality of pores and by providing a guide for the axons as the axons elongate during the nerve regeneration process.

DESCRIPTION OF THE INVENTION

For a better understanding of the present invention, reference is made to the following detailed description taken in conjunction with the appended claims and accompanying drawings. Briefly, the present invention relates to a device for the treatment of central or peripheral nerve injuries. More particularly, the present invention is directed to a tubular membrane that may be used for the treatment of the central or peripheral nerve injuries.

Figure 1:
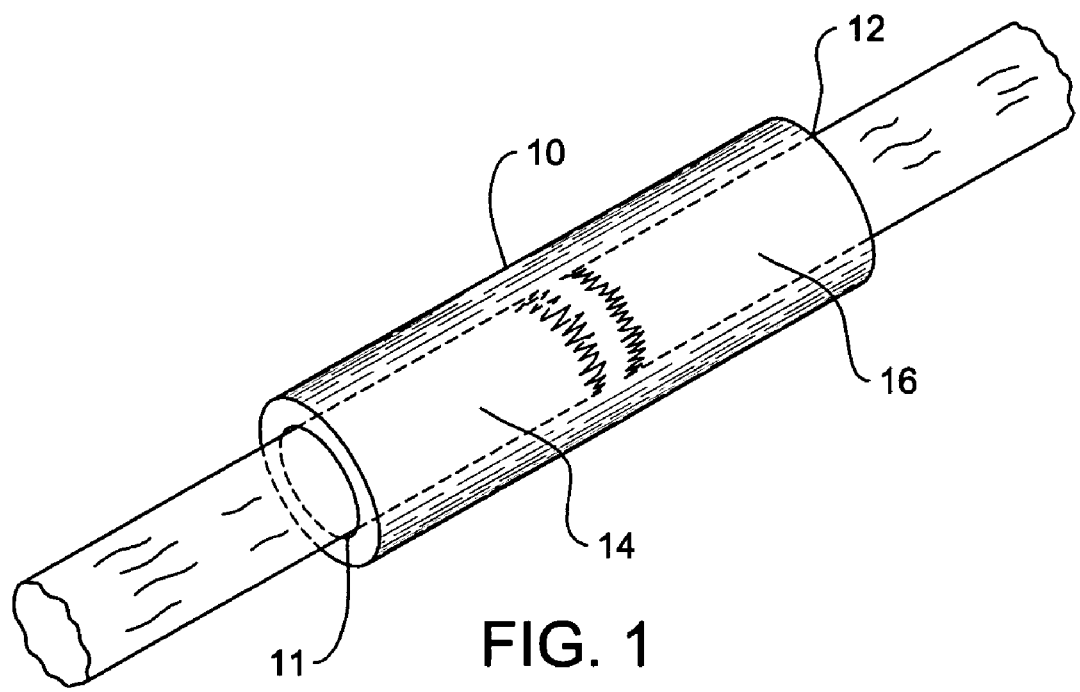
FIG. 1 is a perspective view of an exemplary embodiment of the present invention.
Figure 2A:
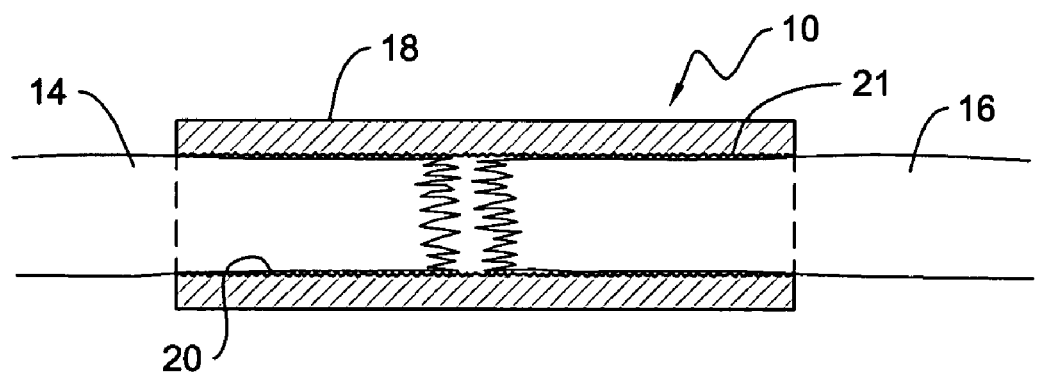
FIG. 2a is a longitudinal cross sectional view of the tubular membrane depicting an exemplary embodiment of the textured surface.
Figure 2B:
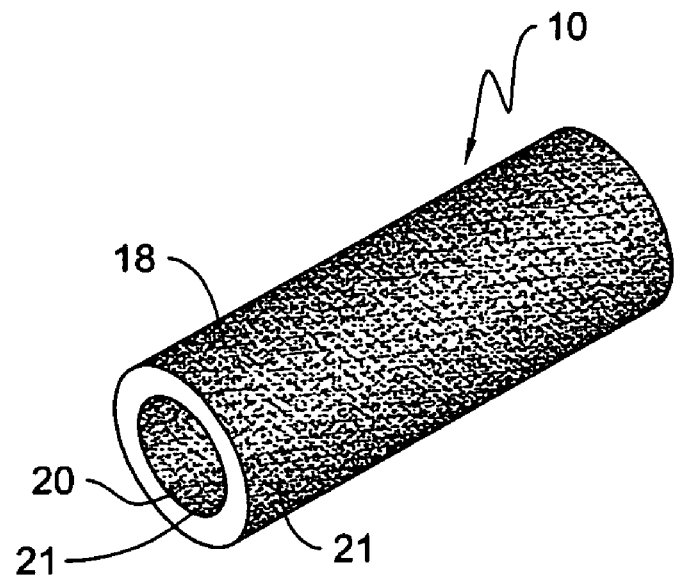
FIG. 2b is a transverse cross sectional view of the tubular membrane depicting an exemplary embodiment of the textured surface.

Referring to FIG. 1, an exemplary embodiment of the present invention comprises a tubular membrane 10 having openings 11, 12 that are configured to receive severed nerve ends 14, 16. As shown in FIGS. 2a and 2b, the tubular membrane has an outer surface 18 and an inner surface 20. The inner surface 20 has a plurality of pores 21 with diameters in the range of 1–3 μm and depths of at least 0.5 μm. Depending on the desired application, the outer surface 18 may also have a plurality of pores 21 with similar diameters in the range of 1–3 μm and depths of at least 0.5 μm. The pores 21 form a microtextured surface or topography. The outer surface 18 and the inner surface 20 may have a single layer of pores 21 or may have multiple layers of pores 21.

Figure 3:
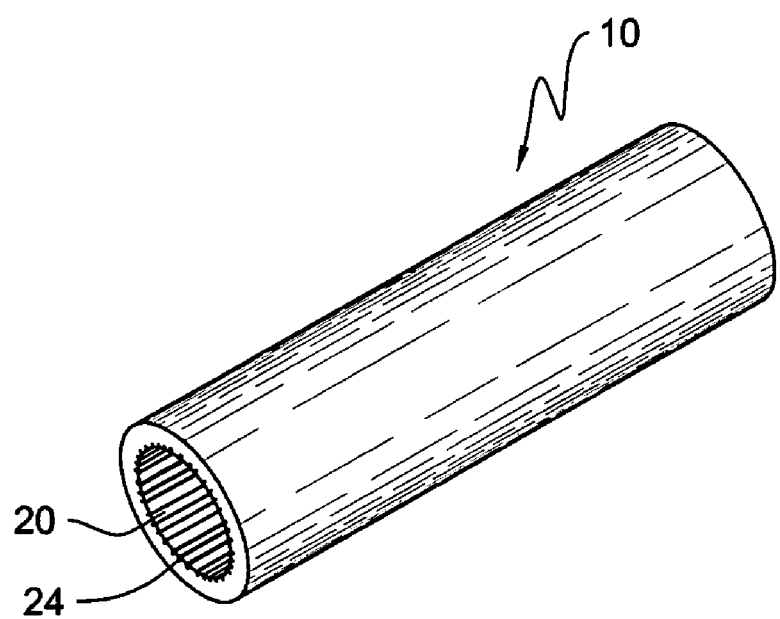
FIG. 3 is a longitudinal cross sectional view of the tubular membrane depicting an exemplary embodiment of the textured surface.

Referring to FIG. 3, the inner surface 20 may also have a plurality of microgrooves or channels 24 that extend lengthwise along the tubular membrane 10 and run parallel to each other. The microgrooves 24 may have widths ranging from 1–3 μm and depths of at least 0.5 μm. The microgrooves 24 serve as conduits and nerve guides for the regeneration of injured or severed nerves ends. Specifically, the microgrooves provide a path or guide for the axons as the axons elongate during the nerve repair process.

In an exemplary embodiment, the tubular membrane 10 has a tubular thickness 22 in the range of 0.002 inch±0.0002 inch, and an inner diameter of approximately 0.5 inches. The thickness and diameter of the membrane may vary depending on the application. For instance, for spinal cord applications, a larger diameter membrane will be required in comparison to peripheral nerve applications where a smaller diameter membrane is needed. In addition, even though the tubular membrane 10 may be constructed of any desirable length, the tubular membrane 10 should have sufficient length so that it will extend about 40 millimeters over the ends 14, 16 of the severed nerve.

The tubular membrane 10 may be constructed of a hollow medical grade titanium rod or other suitable material. In an exemplary embodiment, the pores 21 are formed on the outer surface 18 and the inner surface 20 by applying and sintering 1–3 μm titanium beads onto the outside surface 18 and the inside surface 20 of the titanium rod. For example, the outer and inner surfaces of a medical grade (99%) titanium hollow rod are uniformly coated with a mixture comprising 1–3 μm titanium beads and 0.5% Klucel. The mixture is uniformly dispersed though a stylet or air sprayer onto the clean, outer and inner surfaces of the titanium rod. The titanium rod is placed in a vacuum furnace (e.g., Brew vacuum furnace) and sintered at 1965° F. for 30 minutes at soak temperature in a 4-hour cycle. An appropriate temperature and time must be provided to secure the titanium powder onto the surfaces. For example, if the sintering temperature decreases, then the soak time and cycle time must increase to ensure proper adherence of the titanium powder onto the surfaces. Likewise, if the sintering temperature increases, then a shorter soak time and cycle time are required. To complete the process, the furnace is allowed to cool to 600° F. and backfilled with argon gas. Multi-layers of pores 21 may be formed on the outer surface 18 and the inner surface 20 by either allowing the coating to dry and recoating prior to sintering or, alternatively, re-coating and sintering each additional coat(s).

In another exemplary embodiment, the tubular membrane 10 may be constructed of metallized polymeric material. Silicone, M48, and Pellethane 80A or other suitable polymers may be used for the tubular membrane 10. In this embodiment, the front and back surfaces of an absorbable or non-absorbable polymeric, flat substrate are metallized through DC magnetron sputter coating of pure medical grade titanium. The sputter coating of the polymeric substrate creates a textured surface 20 with pores 21 having diameters in the range of 1–3 μm and depths at least 0.5 μm. In addition, microgrooves or channels 24 having widths ranging from 1–3 μm and depths at least 0.5 μm may be formed on the front and back surfaces of the substrate by making impressions or small cuts with a sharp razor blade or a similar device. The metallized substrate is rolled into a tubular membrane 10 having an appropriate diameter.

To further promote nerve fiber reattachment, neurotrophic and nerve regenerating/growth promoting agents, anti-inflammatory agents, and other antibacterial agents may be coated or embedded in the tubular membrane 10. For example, the tubular membrane 10 may be loaded with a fibrin matrix enriched with nerve regenerating factors such as laminin, vitronectin, or laminin glycoproteins. The fibrin matrix is loaded into the tubular membrane 10 in such a way as to achieve effective neurotrophic concentration at the site of the injury by a slow release mechanism. This is accomplished by blending or dip coating the fibrin agent with a neurotrophic or nerve regenerating agent. Alternatively, the fibrin matrix may be enriched with the neurotrophic or nerve regenerating agents through solvent or ethanol deposition or through covalent bonding. The slow release mechanism is achieved through a gradual release of a concentration of neurotrophic or nerve regenerating agent across a cap or barrier coated matrix.

The present invention also includes a method for achieving in vivo regeneration to achieve interconnection of the severed nerve ends 14, 16. This is accomplished by surgically cutting open the vertebrae bony housing, placing the severed nerve ends in the openings 11, 12 of the tubular membrane 10, and bringing the ends 14, 16 in close proximity to each other. As the tissue repair process progresses, exuberant tissue overgrowth is diverted into the pores 21 of the tubular membrane 10. As a result, tissue overgrowth at the site of injury is prevented from interfering with the regeneration and growth of the nerve. In addition, neurotrophic factors introduced into the tubular membrane 10 will promote nerve growth. Also, the microgrooves or channels 24 provide a path or guide for the regenerating nerve as the nerve ends 14, 16 extend or grow toward each other.

In the foregoing specification, the present invention has been described with reference to specific exemplary embodiments thereof. It will be apparent to those skilled in the art, that a person understanding this invention may conceive of changes or other embodiments or variations, which utilize the principles of this invention without departing from the broader spirit and scope of the invention. The specification and drawings are, therefore, to be regarded in an illustrative rather restrictive sense.

We claim:

1. A device for the treatment of a damaged nerve comprising:
    a solid, non-permeable tubular membrane having an outer surface and an inner surface; and
    a textured surface on the outer surface and the inner surface of the solid tubular membrane, the textured surface including a plurality of pores having diameters between 1–3 μm and depths of at least 0.5 μm
    whereby the device facilitates regeneration of the damaged nerve by diverting fibrous tissue overgrowth into the plurality of pores.

2. The device of claim 1 wherein the textured surface further includes a plurality of channels having widths between 1–3 μm and depths of at least 0.5 μm whereby the channels provide a guide for axons as the axons elongate during the nerve regeneration process.

3. The device of claim 2 wherein the tubular membrane comprises an inner surface and the textured surface is further provided on the inner surface of the tubular membrane.

4. The device of claim 1 wherein a fibrin matrix is embedded on the textured surface of the tubular membrane.

5. The device of claim 4 wherein the fibrin matrix contains a neurotrophic agent.

6. The device of claim 4 wherein the fibrin matrix contains an anti-inflammatory agent.

7. The device of claim 4 wherein the fibrin matrix contains an anti-bacterial agent.

8. A device for the treatment of a damaged nerve comprising a solid, non-permeable tubular titanium membrane having an inner surface and an outer surface, the inner surface and outer surface having a textured topography formed from a plurality of pores and a plurality of channels, the tubular membrane having a first end and a second end for receiving ends of a severed nerve, whereby the tubular titanium membrane facilitates regeneration of the damaged nerve by diverting fibrous tissue overgrowth into the plurality of pores.

9. The device of claim 8 wherein the pores have diameters between 1–3 μm and depths of at least 0.5 μm and the channels have widths between 1–3 μm and depths of at least 0.5 µm, whereby the channels provide a guide for axons as the axons elongate during the nerve regeneration process.

10. A tubular membrane for the treatment of a damaged nerve comprising:
  a solid, non-permeable substrate formed of polymeric material; and
  a metallized coating on the surface of the polymeric substrate, the metallized coating including a plurality of pores with diameters between 1–3 µm and depths of at least 0.5 µm
  whereby the tubular membrane facilitates regeneration of the damaged nerve by diverting fibrous tissue overgrowth into the plurality of pores.

11. The tubular membrane of claim 10 wherein the metallized coating further includes a plurality of channels with widths between 1–3 µm and depths of at least 0.5 µm, whereby the channels provide a guide for axons as the axons elongate during the nerve regeneration process.

12. The tubular membrane of claim 11 further comprising a fibrin matrix embedded in the metallized coating.

13. The tubular membrane of claim 12 wherein the fibrin matrix contains a neurotrophic agent.

14. The device of claim 12 wherein the fibrin matrix contains an anti-inflammatory agent.

15. The device of claim 12 wherein the fibrin matrix contains an anti-bacterial agent.

16. A method of treating a damaged nerve comprising the steps of:
  providing a solid, non-permeable tubular membrane with a textured surface on an outer and an inner surface, the textured surface comprises a plurality of pores having diameters between 1–3 µm and depths of at least 0.5 µm; and
  placing a damaged nerve within the tubular membrane, whereby the tubular membrane facilitates regeneration of the damaged nerve by diverting fibrous tissue overgrowth into the plurality of pores.

17. The method of claim 16 wherein the textured surface on the inner surface further comprises a plurality of channels having widths between 1–3 µm and depths of at least 0.5 µm, whereby the channels provide a guide for axons as the axons elongate during the nerve regeneration process.

* * * * *